US008208992B2

(12) United States Patent
Goto et al.

(10) Patent No.: US 8,208,992 B2
(45) Date of Patent: Jun. 26, 2012

(54) IMAGE DIAGNOSIS SUPPORT DEVICE AND IMAGE DIAGNOSIS SUPPORT PROGRAM

(75) Inventors: Yoshihiro Goto, Tokyo (JP); Suzushi Kusano, Ibaraki (JP)

(73) Assignee: Hitachi Medical Corporation, Tokyo (JP)

( * ) Notice: Subject to any disclaimer, the term of this patent is extended or adjusted under 35 U.S.C. 154(b) by 771 days.

(21) Appl. No.: 12/304,051

(22) PCT Filed: Jun. 4, 2007

(86) PCT No.: PCT/JP2007/061264
§ 371 (c)(1),
(2), (4) Date: Dec. 9, 2008

(87) PCT Pub. No.: WO2007/145093
PCT Pub. Date: Dec. 21, 2007

(65) Prior Publication Data
US 2010/0249580 A1    Sep. 30, 2010

(30) Foreign Application Priority Data
Jun. 12, 2006  (JP) .................................. 2006-162499

(51) Int. Cl.
*A61B 5/055* (2006.01)
*G06K 9/00* (2006.01)
(52) U.S. Cl. ........................................ 600/425; 382/131
(58) Field of Classification Search .................. None
See application file for complete search history.

(56) References Cited

U.S. PATENT DOCUMENTS 6,282,307 B1 * 8/2001 Armato et al. ................ 382/132
6,483,934 B2 * 11/2002 Armato et al. ................ 382/132
6,577,752 B2 * 6/2003 Armato et al. ................ 382/131
(Continued)

FOREIGN PATENT DOCUMENTS
JP        2005-65845        3/2005

OTHER PUBLICATIONS

Tachibana, Rie, et al., "Segmentation of Small Pulmonary Nodules on Thoracic CT Images", *The Transactions of the Institute of Electronics, Information and Communications Engineers*, Jan. 1, 2004, vol. J87-D-II, No. 1, pp. 228-236.

(Continued)

*Primary Examiner* — Long V. Le
*Assistant Examiner* — Angela M Hoffa
(74) *Attorney, Agent, or Firm* — Cooper & Dunham LLP

(57) ABSTRACT

An image diagnosis support device 10 includes an image acquisition section 61 which acquires a tomographic image including a desired organ of an object from a medical image scanning apparatus 2 or a magnetic disk 13; a reference region extraction section 62 which extracts a reference region representing a reference in the organ of interest from the tomographic image acquired by the image acquisition section 61; an organ region extraction section 63 which extracts an organ region representing a region of the organ of interest from the tomographic image acquired by the image acquisition section 61; an organ shape information calculation section 64 which calculates organ shape information regarding the shape of the organ of interest from the reference region extracted by the reference region extraction section 62 and the organ region extracted by the organ region extraction section 63; and display control section 11 which displays on a monitor 15, which is a display device, the organ shape information calculated by the organ shape information calculation section 64.

13 Claims, 9 Drawing Sheets

U.S. PATENT DOCUMENTS

| | | | |
|---|---|---|---|
| 6,724,925 B2 * | 4/2004 | Armato et al. | 382/132 |
| 6,813,375 B2 * | 11/2004 | Armato, III et al. | 382/131 |
| 2001/0021264 A1 * | 9/2001 | Armato et al. | 382/132 |
| 2002/0191827 A1 | 12/2002 | Armato, III et al. | |
| 2003/0086599 A1 | 5/2003 | Armato, III et al. | |
| 2007/0165952 A1 * | 7/2007 | Goto | 382/199 |
| 2008/0298658 A1 * | 12/2008 | Nakashima et al. | 382/131 |
| 2008/0317322 A1 * | 12/2008 | Acharyya et al. | 382/132 |
| 2009/0052754 A1 * | 2/2009 | Goto et al. | 382/128 |
| 2010/0189332 A1 * | 7/2010 | Goto et al. | 382/131 |

OTHER PUBLICATIONS

Tomoda, Itaru, et al., "Computer-aided Detection of Coronary Artery Calcification Using Low Dose Thoracic 3-D CT Images", *IEICE Technical Report*, Sep. 15, 2005, vol. 105, No. 303, pp. 81-85.

*IEEJ Journal*, vol. 124, No. 6, 2004, pp. 349-352.

Apr. 15, 2011 European search report in connection with counterpart European patent application No. 07 74 4649.

Nov. 22, 2011 Japanese official action in connection with a counterpart Japanese patent application.

* cited by examiner

IMAGE DIAGNOSIS SUPPORT DEVICE AND IMAGE DIAGNOSIS SUPPORT PROGRAM

TECHNICAL FIELD

The present invention relates to an image diagnosis support device, and more particularly to an image diagnosis support device and an image diagnosis support program which detect a deformed state a specific organ, such a thickened portion of the thoracic wall.

BACKGROUND ART

In the case of a conventional image diagnosis support device, an operator manually designates points or a region on a medical image in order to perform measurement of a distance or an area (see, for example, "Patent Document 1").
Patent Document 1: Japanese Patent Application Laid-Open (kokai) No. 2005-65845

In recent years, diseases caused by inhalation of asbestos have become a social issue. A person who has inhaled a large mount of asbestos tends to have an increased thoracic wall thickness. Such an anomaly of thoracic wall thickness is visually found by a medical doctor. However, the medical doctor may overlook such anomaly, in some instances, in a visual inspection.

That is, there is an unsolved problem in the conventional image diagnosis support device in that a medical doctor encounters difficulty in finding an anomalous site in a case where an anomaly does not appear on all tomographic images and only a portion of the tomographic images are observed.

BRIEF SUMMARY

In an aspect of this disclosure, there are provided an image diagnosis support device and an image diagnosis support program which allow a medical doctor to readily find an anomalous site.

In another aspect of this disclosure, there is provided an image diagnosis support device comprising image acquisition means for acquiring a tomographic image including a desired organ of an object to be examined; reference region extraction means for extracting a reference region representing a reference in the organ of interest from the tomographic image acquired by the image acquisition means; organ region extraction means for extracting an organ region representing a region of the organ of interest from the tomographic image acquired by the image acquisition means; organ shape information calculation means for calculating organ shape information regarding the shape of the organ of interest from the reference region extracted by the reference region extraction means and the organ region extracted by the organ region extraction means; and display control means for displaying on a display device the organ shape information calculated by the organ shape information calculation means.

Further, in another aspect there is provided an image diagnosis support program that causes a computer to execute an image acquisition step of acquiring a tomographic image including an organ of interest of an object; a reference region extraction step of extracting a reference region representing a reference in the organ of interest from the tomographic image acquired by the image acquisition step; an organ region extraction step of extracting an organ region representing the organ of interest from the tomographic image acquired by the image acquisition step; an organ shape information calculation step of calculating organ shape information regarding the shape of the organ of interest from the reference region extracted by the reference region extraction-step and the organ region extracted by the organ region extraction step; and a display control step of displaying on a display device the organ shape information calculated by the organ shape information calculation step.

Thus, shape information regarding an extracted organ region is displayed on a screen, an image diagnosis support device and an image diagnosis support program can be provided to allow a medical doctor to readily find an anomalous site.

DESCRIPTION OF REFERENCE NUMERALS

Figure 1:
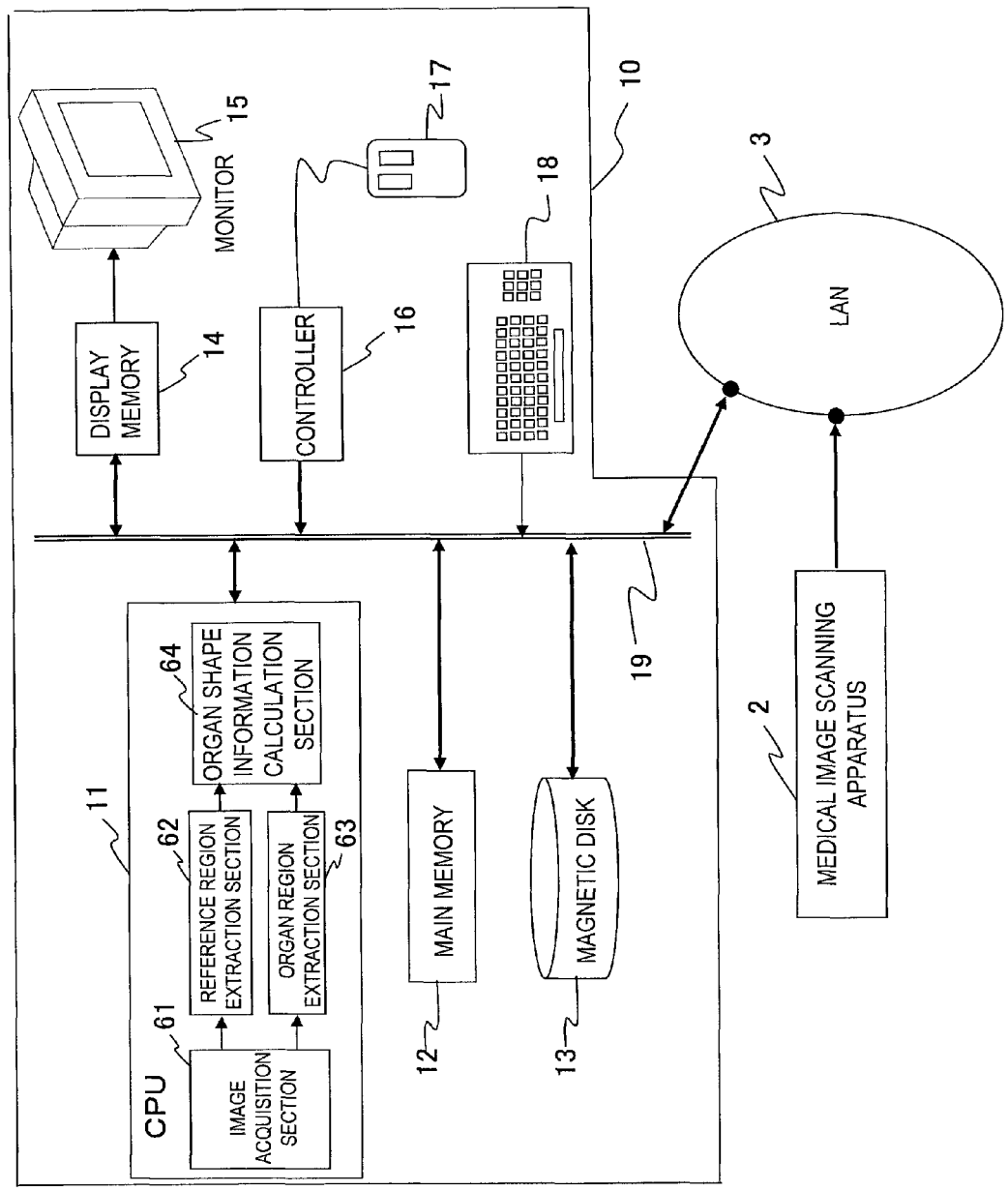
FIG. 1 Hardware configuration diagram showing the configuration of an image diagnosis support device.

10: image diagnosis support device
11: CPU
12: main memory
13: magnetic disk
14: display memory
15: monitor
16: controller
17: mouse
18: keyboard
19: common bus
20A and 20B: ribs
22A and 22B: rib ends
30A and 30B: lung fields
32A and 32B: centroids of lung fields
34A and 34B: reference lines
71 and 72: axial image
73: three-dimensional image

BEST MODE FOR CARRYING OUT THE INVENTION

Preferred embodiments of the present invention will now be described in detail with reference to the accompanying drawings. In the following description and accompanying drawings, structural elements having like functions are denoted by like reference numerals, and their descriptions will not be repeated.

FIG. 1 is a hardware configuration diagram showing the configuration of an image diagnosis support device 10.

The image diagnosis support device 10 is connected to a medical image scanning apparatus 2, which scans an image of an object, via a network such as a LAN 3.

The medical image scanning apparatus 2 scans a medical image of the object. Examples of the medical image scanning apparatus 2 include an X-ray CT apparatus, an MR apparatus, and an ultrasonic image scanning apparatus. However, the medical image scanning apparatus 2 is not limited thereto, and any other apparatus can be selectively used, so long as the selected apparatus can scan a medical image of an object.

In the image diagnosis support device 10, a CPU (Central Processing Unit) 11, a main memory 12, a magnetic disk 13, a display memory 14, a monitor (display) 15, a controller 16, a mouse 17, and a keyboard 18 are connected with one another via a common bus 19.

The CPU 11 is a control device for controlling operations of the various components. The main memory 12 stores a control program of the device, and provides a working area used when the program is executed. The magnetic disk 13 stores an operating system (OS), device drives for peripheral devices, and various application software programs, including a program for performing various types of processing such as measurement of the thickness of an organ wall. The magnetic disk 13 also receives, via a network such as the LAN 3, medical images scanned by the medical image scanning apparatus 2, and stores them. Notably, the CPU 11 reads each of the programs out of the magnetic disk 13, loads them into the main memory 12, and then executes them.

The display memory 14 temporarily stores data to be displayed. The display 15 is a CRT monitor, a liquid crystal monitor, or a like monitor, which displays an image on the basis of the data from the display memory 14. The mouse 17 is connected to the controller 16. The controller 16 transmits via the common bus 19 to the CPU 11 information input by an operator through the mouse 17. The mouse 17 is a device for entering information regarding a position on the screen of the display 15 desired by the operator, and an input command present at the desired position. The keyboard 18 enables the operator not only to enter information regarding the designated position on the screen of the display 15 as in the case of the mouse 17, but also to enter conditions under which the display 15 displays an image or the like. The common bus 19 connects the above-described constituent elements such that they can transfer data mutually.

The CPU 11 of the image diagnosis support device 10 includes an image acquisition section 61, a reference region extraction section 62 and an organ region extraction section 63 connected to the image acquisition section 61, and an organ shape information calculation section 64 connected to the reference region extraction section 62 and the organ region extraction section 63.

The image acquisition section 61 is connected to the mouse 17 and the keyboard 18 via the common bus 19. The reference region extraction section 62, the organ region extraction section 63, and the organ shape information calculation section 64 are connected to the display memory 14 via the common bus 19.

The image acquisition section 61 acquires a medical image from the medical image scanning apparatus 2 via the LAN 3, and stores it in the magnetic disk 13. Notably, the term "medical image" must be broadly interpreted so as to encompass not only the medical image scanned by the medical image scanning apparatus 2, but also secondary medical images (e.g., a quasi three-dimensional image and a developed image) obtained by performing image processing on the medical image.

The reference region extraction section 62 extracts a reference region. The reference region is a region which serves as a reference of information regarding the shape of an organ to be measured (hereinafter referred to as "organ shape information"). Organ shape information in a normal state may be used as the reference region. The reference region extraction section 62 may extract the reference region by performing threshold processing on the medical image acquired by the image acquisition section 61, on the basis of pixel values, CT values, or gray levels thereof. When the thickness of the thoracic wall is measured as the organ shape information, the reference region extraction section 62 may extract the reference region by detecting a region of ribs. The region of the ribs itself may be used as the reference region, or the reference region may be determined such that the reference region includes the ribs and a region (e.g., a region corresponding to a few pixels) near the ribs. Alternatively, the reference region may be determined by connecting end portions of the ribs (including a thin film covering the ribs) or points near the end portions.

The organ region extraction section 63 extracts a region of the organ to be measured by performing threshold processing, on the medical image acquired by the image acquisition section 61, on the basis of pixel values, CT values, or gray levels thereof. Further, the organ region extraction section 63 calculates information (thickness, length, area, volume, etc.) which partially relates to the shape of the organ. Notably, the threshold values used in the processing for extracting the reference region and the organ region may be properly determined on the basis of the threshold value used in the processing for extracting the bone region.

The organ shape information calculation section 64 obtains the organ shape information for the entire organ to be measured, on the basis of the reference region extracted by the reference region extraction section 62 and the organ region extracted by the organ region extraction section 63. The organ shape information is information regarding the shape of an organ, such as thickness, length, area, volume, etc., and no limitation is imposed on the type or dimension of the information. For example, the organ shape information may be the thickness of the thoracic wall. The organ shape information calculation section 64 obtains outer shape information, such as the thickness of the thoracic wall, by calculating the difference between the outer shape of the thoracic region and the outer shape of the reference region.

Next, various embodiments will be described with reference to the drawings. Here, there will be described a case in which an axial image including the lung regions is used as a medical image including an organ region, and the thickness of the thoracic wall is measured.

<First Embodiment>

A first embodiment will be described with reference to FIGS. 2 to 7.

Figure 2:
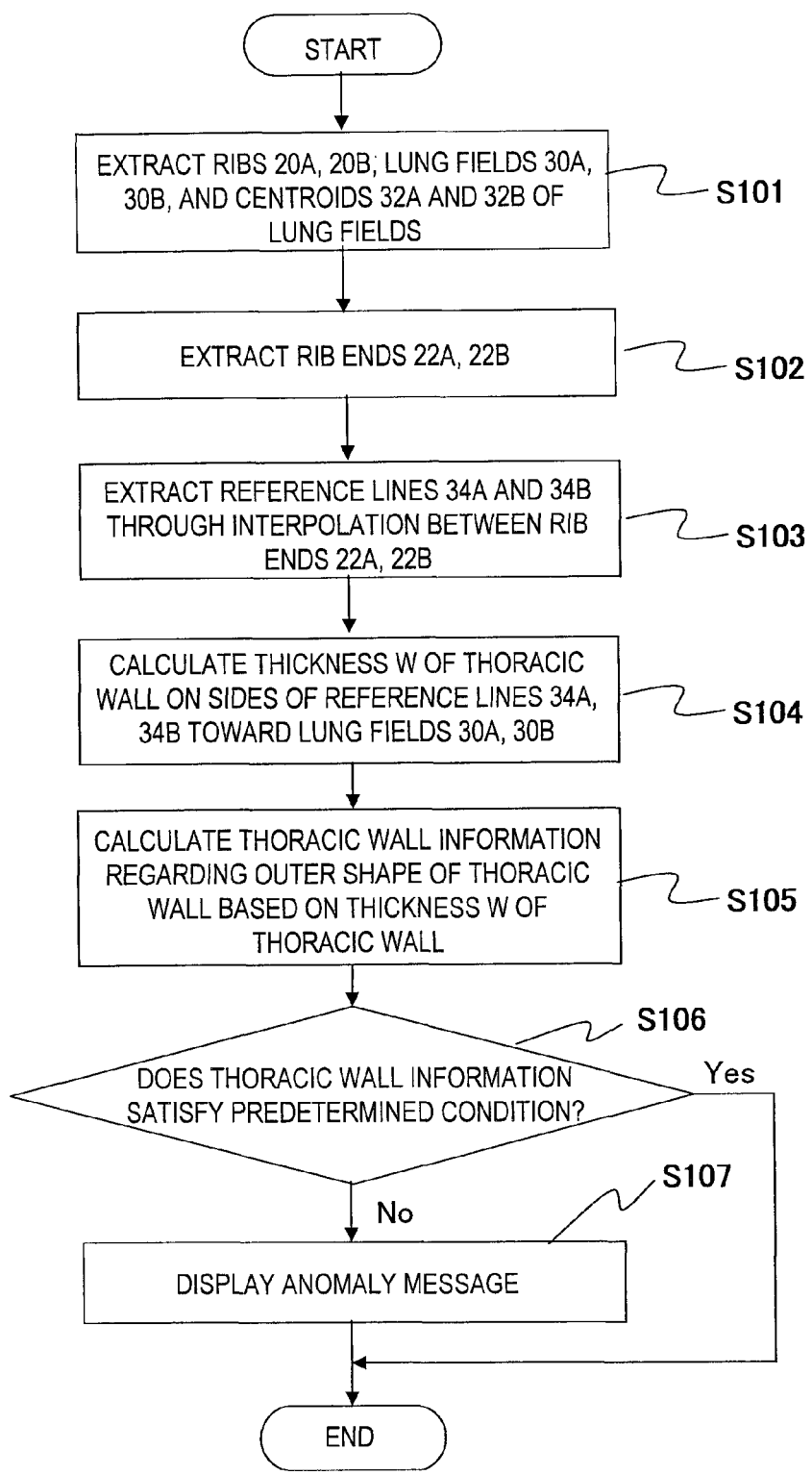
FIG. 2 Flowchart showing the processing of the image diagnosis support device.

FIG. 2 is a flowchart showing the processing of the image diagnosis support device.

The CPU 11 (the image acquisition section 61) acquires, from the medical image scanning apparatus 2 or the magnetic disk 13, a medical image (an axial image, a three-dimensional image, or the like) obtained by scanning the lungs of an object; and develops the medical image in the main memory 12.

(Step S101)

Figure 3:
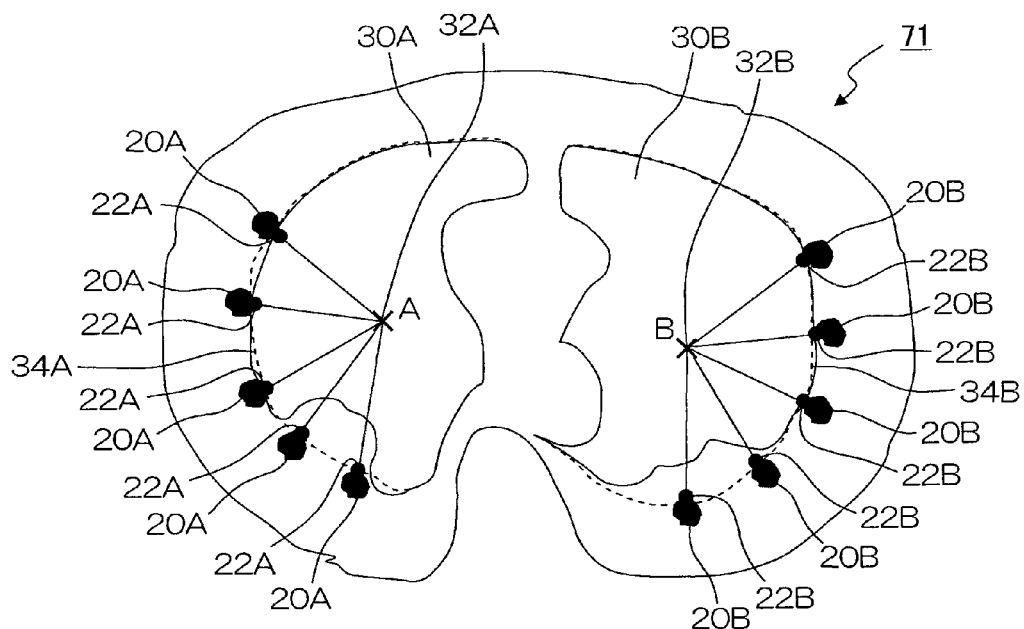
FIG. 3 Explanatory chart showing a method of obtaining a reference line when the thickness of a thoracic wall is calculated.

FIG. 3 is an explanatory chart showing a method of obtaining a reference line when the thickness of a thoracic wall is calculated.

The CPU 11 (the reference region extraction section 62) performs threshold processing on an axial image 71 developed in the main memory 12, to thereby extract left and right ribs 20A and 20B. The CPU 11 (the organ region extraction section 63) performs threshold processing on the axial image 71 developed in the main memory 12, to thereby extract lung fields 30A and 30B. In the threshold processing, a threshold regarding CT values, gray levels, or pixel values is set for the axial image 71, whereby region extraction is performed.

(Step S102)

Figure 4:
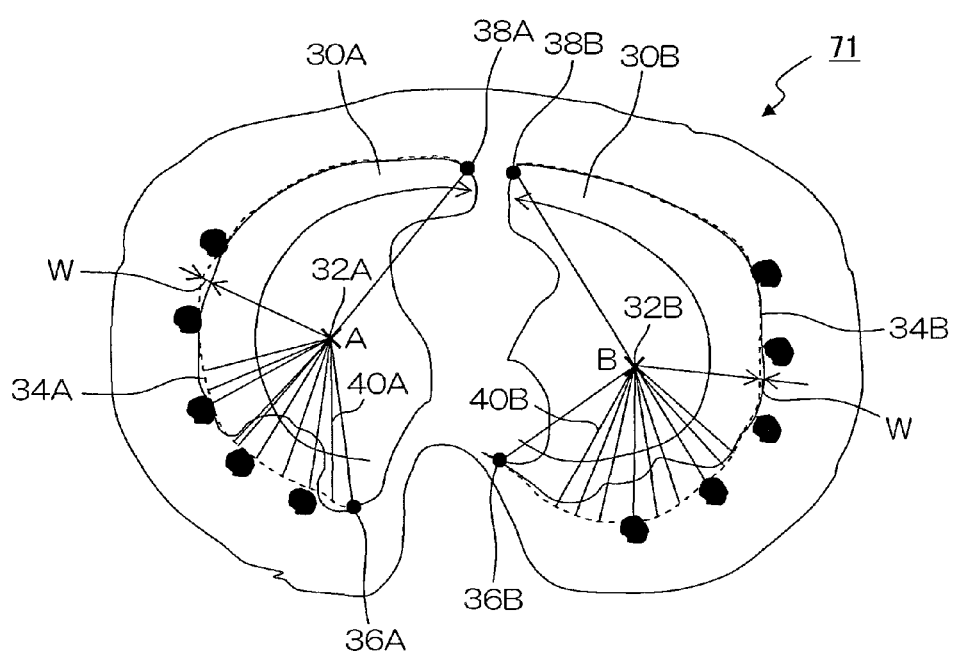
FIG. 4 Explanatory chart showing a method of calculating the thickness of the thoracic wall.

FIG. 4 is an explanatory chart showing a method of calculating the thickness of the thoracic wall.

The CPU 11 (the organ region extraction section 63) calculates the centroids 32A and 32B of the lung fields 30A and 30B. The CPU 11 (the reference region extraction section 62) calculates, as rib ends 22A and 22B, points closest to the centroids 32A and 32B of the lung fields 30A and 30B, among the points on the outer circumferences of the ribs 20A and 20B.

(Step S103)

The CPU 11 (the reference region extraction section 62) connects the rib ends 22A and the rib ends 22B by means of interpolation curves such as spline curves, to thereby obtain reference lines 34A and 34B. The reference lines 34A and 34B correspond to a reference region in measurement of thickness of the thoracic wall.

(Step S104)

The CPU 11 (the organ region extraction section 63) connects the centroid 32A of the lung field 30A and a back-side point 36A on the reference line 34A by a straight line 40A. Similarly, the CPU 11 (the organ region extraction section 63) connects the centroid 32B of the lung field 30B and a back-side point 36B on the reference line 34B by a straight line 40B. The CPU 11 (the organ region extraction section 63) performs the threshold processing along the straight lines 40A and 40B so as to calculate the thickness W of the thoracic wall at the back-side points 36A and 36B. The CPU 11 (the organ shape information calculation section 64) performs the above-described processing from the back-side point 36A to a front-side point 38A along the reference line 34A and from the back-side point 36B to a front-side point 38B along the reference line 34B, to thereby calculate the thickness W of the thoracic wall for the entirety of the thoracic wall.

(Step S105)

The CPU 11 (the organ shape information calculation section 64) calculates thoracic wall information regarding the outer shape of the thoracic wall on the basis of the thickness W of the thoracic wall. Notably, in the first embodiment, the thickness W of the thoracic wall itself is treated as thoracic wall information.

(Step S106)

Figure 5:
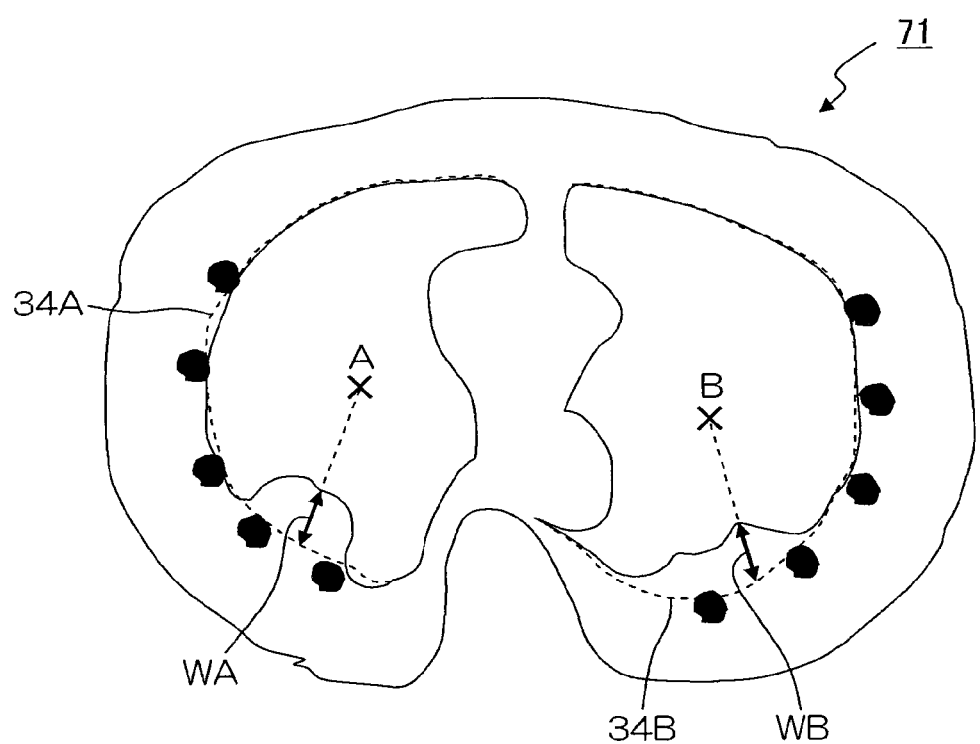
FIG. 5 Explanatory chart showing a method of calculating the thickness of the thoracic wall.

FIG. 5 is an explanatory chart showing a method of calculating the thickness of the thoracic wall.

The CPU 11 determines whether or not the thoracic wall information satisfies a predetermined condition. In the first embodiment, the CPU 11 determines whether or not both the maximum values WA and WB of the thickness W of the thoracic wall are less than a predetermined value W'.

(Step S107)

Figure 6:
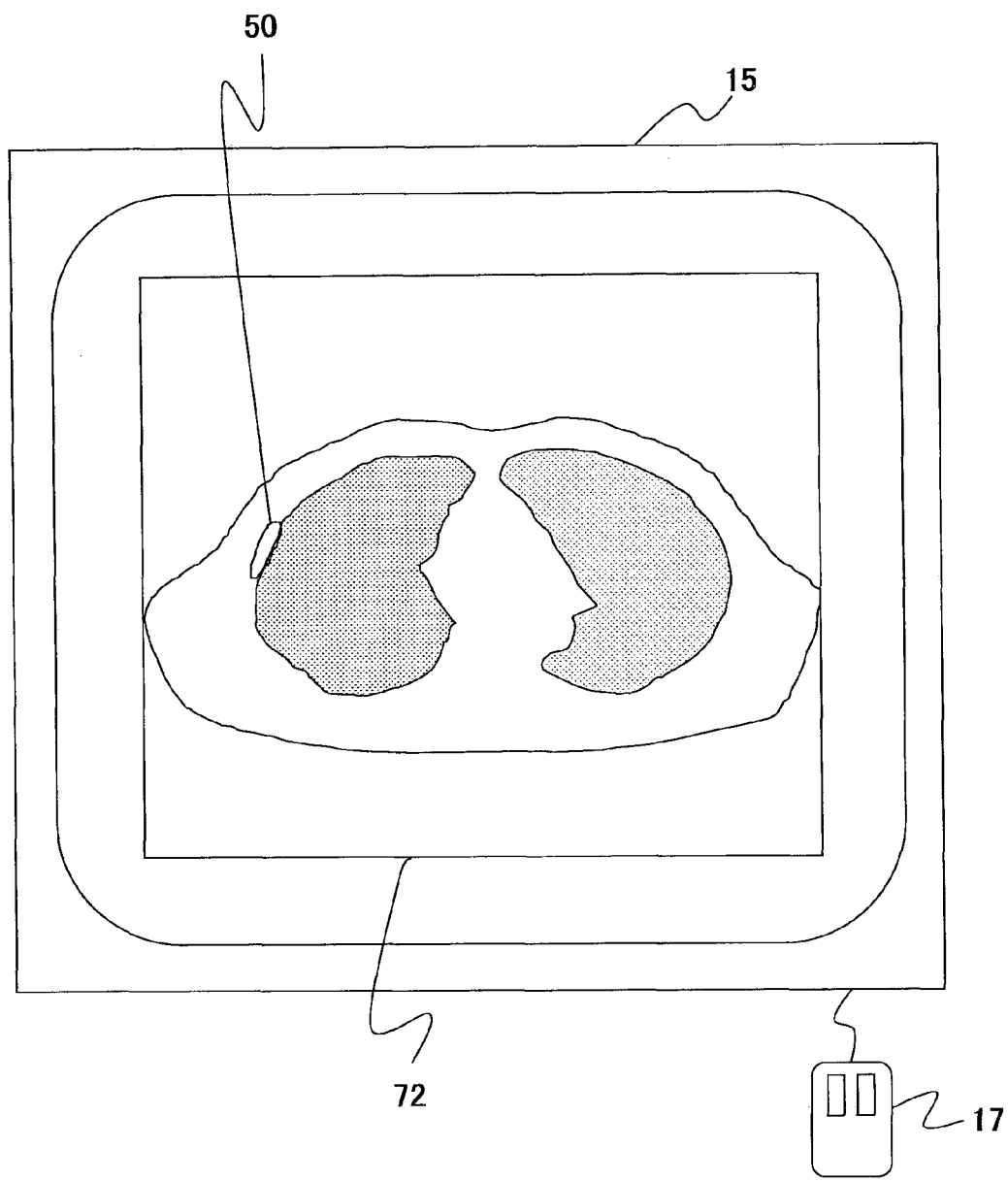
FIG. 6 Illustration showing an example image display screen.

FIG. 6 is an illustration showing an example image display screen.

When the CPU 11 determines that the thoracic wall information satisfies the predetermined condition, the CPU 11 ends the processing (Yes in step S106). When the CPU 11 determines that the thoracic wall information does not satisfy the predetermined condition, the CPU 11 performs warning processing (No in step S106). The CPU 11 displays on the monitor 15 a warning display 50 which is a solid line surrounding an anomalous portion, along with an axial image 72. Notably, the warning processing is not limited to the above-described warning display 50, so long as the anomaly portion can be identified. For example, the anomaly portion may be made clear by displaying the anomaly portion in an anomaly color such as red.

Figure 7:
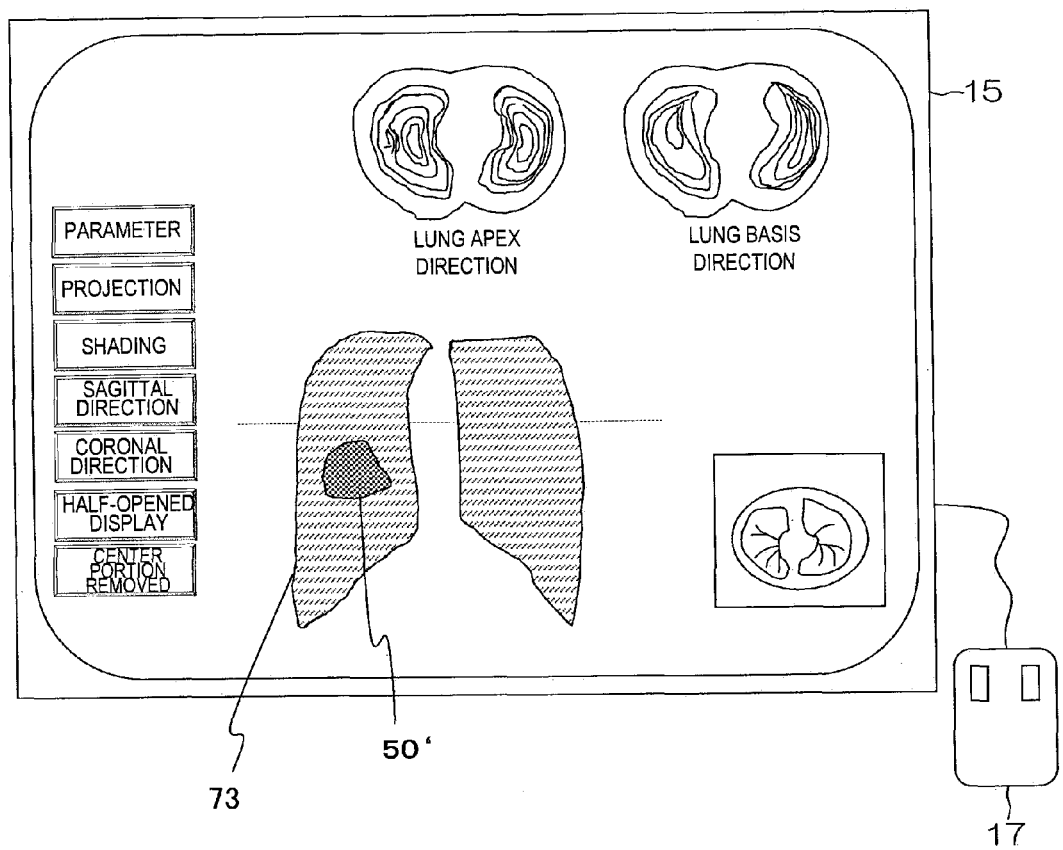
FIG. 7 Illustration showing an example image display screen.

FIG. 7 is an illustration showing an example image display screen.

In FIG. 6, the warning display 50 is displayed along with the axial image 72. In contrast, in FIG. 7, a warning display 50' is displayed on a three dimensional image 73. Further, a message, such as "suspected of suffering from mesothelioma" may be displayed on the display screen. Although the warning color of the warning display 50' of FIG. 7 is red, the warning color is not limited to red. Further, the anomalous portion may be surrounded by a solid line as in the case of FIG. 6.

According to the first embodiment, an anomaly of the thoracic wall can be found through detection of a location where the thoracic wall has an increased thickness, whereby the doctor's attention can be called. Since the shape information of the extracted organ region is displayed on the screen, finding of an anomalous site by the doctor can be facilitated. Further, the effect peculiar to the first embodiment is that since the thickness of the thoracic wall can be calculated automatically, operation load can be reduced, and variation of measurement results can be suppressed to thereby improve measurement accuracy.

Notably, in the above-described embodiment, a medical image (an axial image, a three-dimensional image, or the like) obtained by scanning the lungs of an object is transferred from the medical image scanning apparatus 2 to the image diagnosis support device 10, and is processed there. However, the embodiment may be modified in such a manner that projection data obtained by scanning the lungs of an object by use of an X-ray CT device or the like are transferred from the medical image scanning apparatus 2 to the image diagnosis support device 10, and a three-dimensional image, an axial image, or the like is reconstructed in the image diagnosis support device 10. Further, in the above-described embodiment, the thickness of the thoracic wall is calculated by use of an axial image. However, a tomographic image such as an MPR (Multi Planar Reconstruction) image may be used in place of the axial image. Further, in the above-described embodiment, the rib ends 22A and the rib ends 22B are connected by smooth interpolation curves through spline interpolation. However, other known interpolation methods may be used. Further, in the above-described embodiment, calculation of the thickness W of the thoracic wall is performed from the back-side points 36A and 36B toward the front-side points 38A and 38B. However, no limitation is imposed on the order of the calculation, so long as the entire thoracic wall can be covered.

For example, the embodiment may be modified as follows. A threshold value for a normal thoracic wall is obtained by use of a density histogram in the vicinity of ribs without performing interpolation processing; a value slightly lower than this threshold value is re-set as a threshold value for an anomalous thoracic wall; and a determination as to whether a thoracic wall is normal or anomalous is made through use of this re-set threshold value.

Further, pixels in a region around each rib may be obtained by extracting a normal thoracic wall; re-setting, as a threshold value, a value (empirical value) lower than the threshold value for the extracted normal thoracic wall; and performing threshold processing by use of this re-set threshold value so as to determine whether or not a measured thoracic wall is anomalous.

<Second Embodiment>

Next, a second embodiment will be described with reference to FIG. 8.

Figure 8:
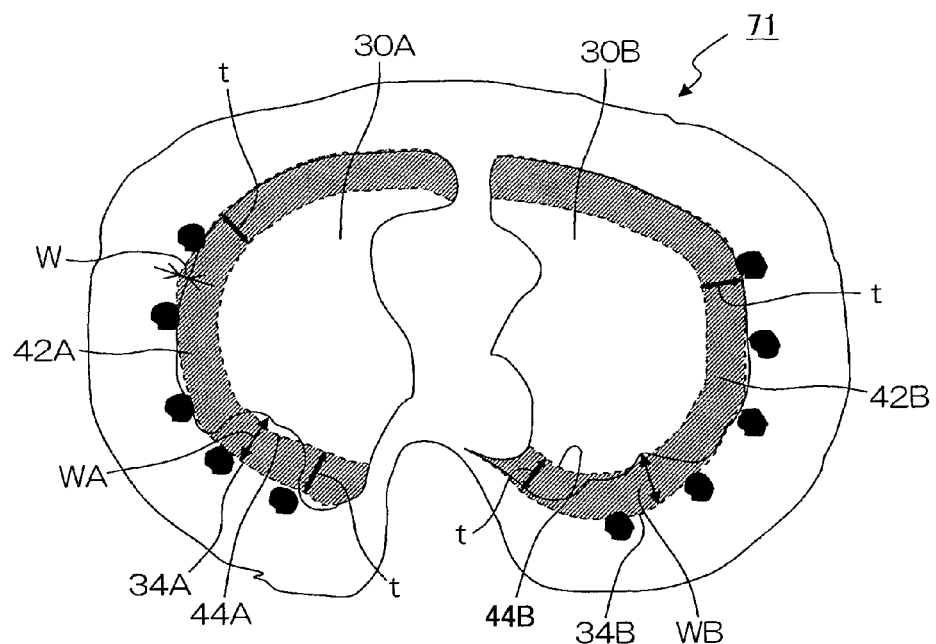
FIG. 8 Explanatory chart showing a method of calculating the thickness of the thoracic wall in a second embodiment.

FIG. 8 is an explanatory chart showing a method of calculating the thickness of the thoracic wall in the second embodiment.

Since the processing of steps S101 to S103 and the processing of steps S105 to S107 are the identical with those of the first embodiment, their description will not be repeated.

In step S104, the processing as described below is performed so as to calculate the thickness W of the thoracic wall as measured on the side of the reference line 34A toward the lung field 30A and as measured on the side of the reference line 34B toward the lung field 30B. The CPU 11 (the organ region extraction section 63) calculates regions 42A and 42B which are surrounded by the reference lines 34A and 34B and lines 44A and 44B, respectively, wherein the lines 44A and 44B are obtained by translating the reference lines 34A and 34B into the lung fields 30A and 30B by a distance t. That is, the regions 42A and 42B are passage regions formed by translating the reference lines 34A and 34B. The CPU 11 (the organ shape information calculation section 64) performs threshold processing on these regions 42A and 42B, to thereby calculate the thickness W of the thoracic wall over the entire thoracic wall.

According to the second embodiment, an anomaly of the thoracic wall can be found through detection of a location where the thoracic wall has an increased thickness, whereby the doctor's attention can be called. Since the shape information of the extracted organ region is displayed on the screen, finding of an anomalous site by the doctor can be facilitated. The second embodiment has a peculiar effect in that the thickness of the thoracic wall can be calculated without calculating the centroids of the lung fields.

<Third Embodiment>

Next, a third embodiment will be described with reference to FIG. 9.

Figure 9:
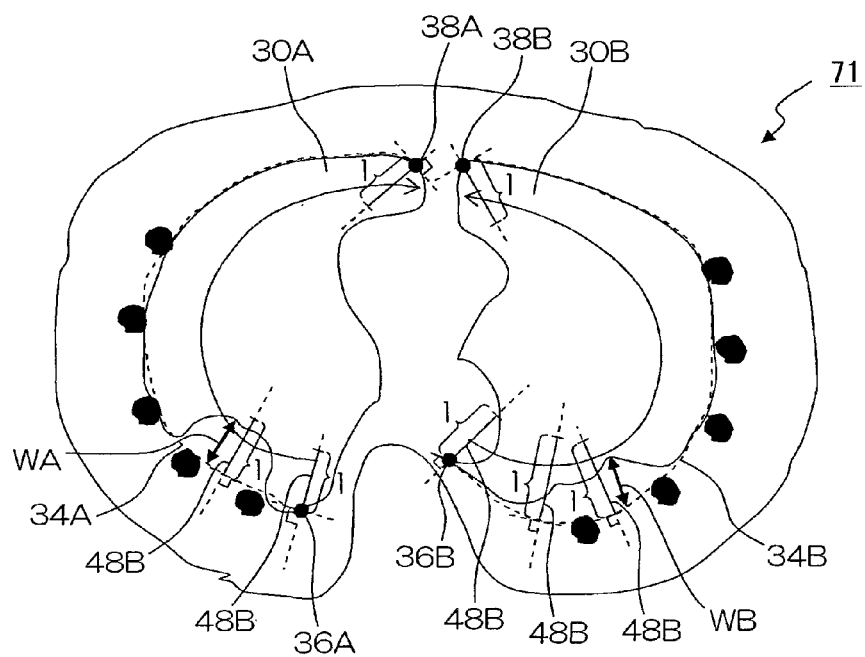
FIG. 9 Explanatory chart showing a method of calculating the thickness of the thoracic wall in a third embodiment.

FIG. 9 is an explanatory chart showing a method of calculating the thickness of the thoracic wall in the third embodiment.

Since the processing of steps S101 to S103 and the processing of steps S105 to S107 are the identical with those of the first embodiment, their description will not be repeated.

In step S104, the processing as described below is performed so as to calculate the thickness W of the thoracic wall as measured on the side of the reference line 34A toward the lung field 30A and as measured on the side of the reference line 34B toward the lung field 30B. The CPU 11 (the organ region extraction section 63) calculates the thickness W of the thoracic wall at the back-side points 36A and 36B on the reference lines 34A and 34B by performing threshold processing along straight lines 48A and 48B which extend along normal lines of the reference lines 34A and 34B from the back-side points 36A and 36B into the lung fields 30A and 30B, respectively, and each of which has a length 1. The CPU 11 (the organ shape information calculation section 64) performs the above-described processing along the reference lines 34A and 34B from the back-side points 36A and 36B to the front-side points 38A and 38B, to thereby calculate the thickness W of the thoracic wall over the entire thoracic wall.

According to the third embodiment, an anomaly of the thoracic wall can be found through detection of a location where the thoracic wall has an increased thickness, whereby the doctor's attention can be called. Since the shape information of the extracted organ region is displayed on the screen, finding of an anomalous site by the doctor can be facilitated. The third embodiment has a peculiar effect in that the thickness of the thoracic wall can be calculated without calculating the centroids of the lung fields or performing the threshold processing in a specific region.

Fourth Embodiment

Next, a fourth embodiment will be described with reference to FIG. 10.

Figure 10:
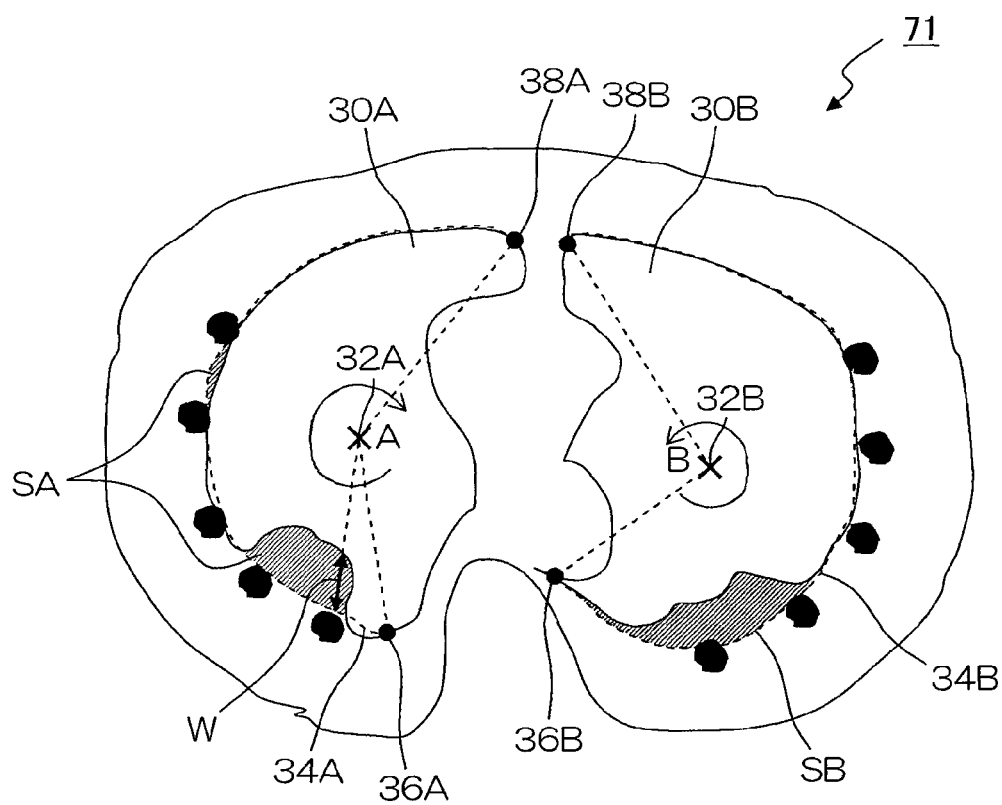
FIG. 10 Explanatory chart showing a method of calculating the thickness of the thoracic wall in a fourth embodiment.

FIG. 10 is an explanatory chart showing a method of calculating the thickness of the thoracic wall in the fourth embodiment.

Since the processing of steps S101 to S104 and the processing of step S107 are the identical with those of the first embodiment, their description will not be repeated.

In step S105, the CPU 11 (the organ shape information calculation section 64) calculates an area S of the thoracic wall on the basis of the thickness W of the thoracic wall. In the fourth embodiment, this area S of the thoracic wall is treated as the thoracic wall information.

The CPU 11 (the organ shape information calculation section 64) calculates, as areas SA and SB of the thoracic wall, the total sums of values of the thickness W of the thoracic wall along the reference lines 34A and 34B from the back-side points 36A and 36B to the front-side points 38A and 38B.

In step 106, the CPU 11 determines whether or not the thoracic wall information satisfies a predetermined condition. In the fourth embodiment, the CPU 11 determines whether or not the area S (SA+SB) of the thoracic wall is less than a predetermined value S'.

According to the fourth embodiment, an anomaly of the thoracic wall can be found through detection of a location where the thoracic wall has an increased thickness, whereby the doctor's attention can be called. Since the shape information of the extracted organ region is displayed on the screen, finding of an anomalous site by the doctor can be facilitated. The fourth embodiment has a peculiar effect in that, through obtaining the area of the thoracic wall, an anomaly of the thoracic wall can be found and a doctor's attention can be called. Diseases caused by inhalation of asbestos are characterized in that the thoracic wall has an elongated thick portion or a plurality of thick portions. The fourth embodiment in which an anomaly of the thoracic wall is found on the basis of the area of the thoracic wall is effective in particular in the case where the thoracic wall has a plurality of thick portions.

Fifth Embodiment

Next, a fifth embodiment will be described with reference to FIG. 11.

Figure 11:
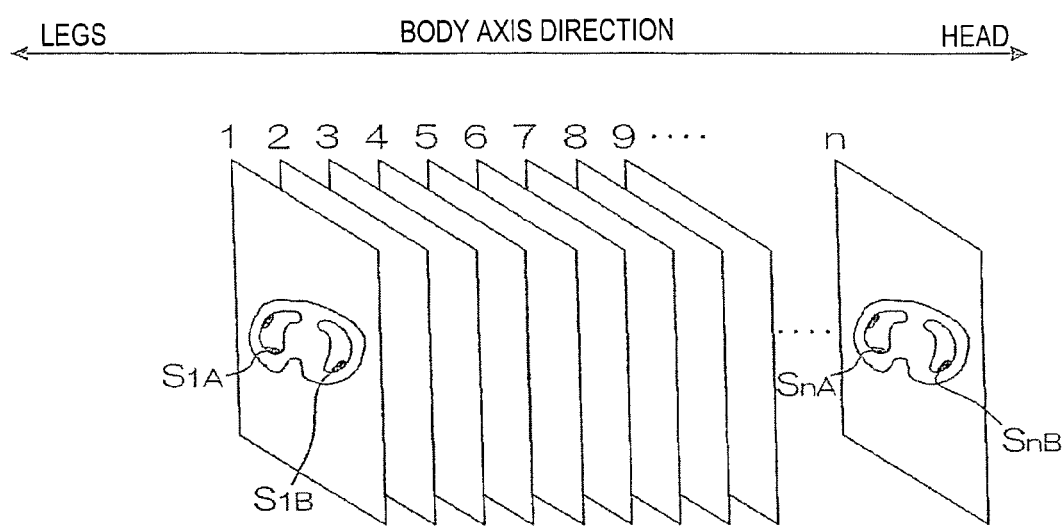
FIG. 11 Explanatory chart showing a method of calculating the thickness of the thoracic wall in a fifth embodiment.

FIG. 11 is an explanatory chart showing a method of calculating the thickness of the thoracic wall in the fifth embodiment.

Since the processing of steps S101 to S104 and the processing of step S107 are identical with those of the first embodiment, their description will not be repeated.

In step S105, the CPU 11 (the organ shape information calculation section 64) calculates a volume V of the thoracic wall on the basis of the area S of the thoracic wall. In the fifth embodiment, this volume V of the thoracic wall is treated as the thoracic wall information.

In the case where n images are produced through scanning the thoracic wall, the CPU 11 (the organ shape information calculation section 64) calculates the volume V of the entire thoracic wall from the area S of the thoracic wall calculated in the fourth embodiment, in accordance with the following equations:

$$VA = (S_{1A} + S_{2A} + \ldots + S_{nA}) \times \Delta x$$

$$VB = (S_{1B} + S_{2B} + \ldots + S_{nB}) \times \Delta x$$

where $S_{1A}$ and $S_{1B}$ represent the areas of the thoracic wall in the first image, $S_{2A}$ and $S_{2B}$, represent the areas of the thoracic wall in the second image, $S_{nA}$ and $S_{nB}$ represent the areas of the thoracic wall in the n-th image, and $\Delta x$ represents the interval between the images.

In step 106, the CPU 11 determines whether or not the thoracic wall information satisfies a predetermined condition. In the fifth embodiment, the CPU 11 determines whether or not the volume V (VA+VB) of the thoracic wall is less than a predetermined value V'.

According to the fifth embodiment, an anomaly of the thoracic wall can be found through detection of a location where the thoracic wall has an increased thickness, whereby the doctor's attention can be called. Since the shape information of the extracted organ region is displayed on the screen, finding of an anomalous site by the doctor can be facilitated. The fifth embodiment has a peculiar effect in that, through obtaining the volume of the thoracic wall, an anomaly of the thoracic wall can be found and a doctor's attention can be called. Diseases caused by inhalation of asbestos are characterized in that the thoracic wall has an elongated thick portion or a plurality of thick portions. The fifth embodiment in which an anomaly of the thoracic wall is found on the basis of the volume of the thoracic wall is effective in the above-described case.

Sixth Embodiment

Next, a sixth embodiment will be described.

In the above-described embodiments, the CPU 11 (the reference region extraction section 62) connects the rib ends 22A and the rib ends 22B by interpolation curves such as spline curves to thereby calculate the reference lines 34A and 34B, which serve as the reference regions in measurement of thoracic wall information. In contrast, in the sixth embodiment, the CPU 11 (the reference region extraction section 62) calculates the reference regions without performing interpolation processing.

The CPU 11 (the reference region extraction section 62) sets a threshold value for extraction of reference regions for the axial image 71, and performs threshold processing, to thereby extract reference regions. The CPU 11 (the organ region extraction section 63) sets a threshold value for extraction of organ regions for the axial image 71, and performs threshold processing, to thereby extract organ regions.

In the case of processing for measurement of the thickness of the thoracic wall, preferably, the threshold value for extraction of reference regions and the threshold value for extraction of organ regions are set on the basis of a threshold value for extraction of ribs.

According to the sixth embodiment, an anomaly of the thoracic wall can be found through detection of a location where the thoracic wall has an increased thickness, whereby the doctor's attention can be called. Since the shape information of the extracted organ region is displayed on the screen, finding of an anomalous site by the doctor can be facilitated. The sixth embodiment has a peculiar effect in that, since the reference regions can be extracted without performing interpolation processing, the measurement accuracy of organ shape information can be improved. Further, for measurement of the thickness of the thoracic wall, extraction of rib regions is not necessarily required.

Seventh Embodiment

Next, a seventh embodiment will be described.

In the above-described embodiments, the CPU 11 (the reference region extraction section 62 and the organ region extraction section 63) automatically extracts the reference regions and the organ regions by performing threshold processing and interpolation processing. In contrast, in the seventh embodiment, the CPU 11 (the reference region extraction section 62 and the organ region extraction section 63) extracts the reference regions and the organ regions via a manual operation of an operator.

When the operator designates one or a plurality of points or regions on the axial image 71 by use of the mouse 17 and the keyboard 18, the CPU 11 (the reference region extraction section 62 and the organ region extraction section 63) performs region extraction processing on the basis of CT values, pixel values, and gray levels in the vicinity of the designated points or regions, to thereby extract the reference regions or the organ regions. For example, a region-growing method or a like method may be used as the region extraction processing.

According to the seventh embodiment, an anomaly of the thoracic wall can be found through detection of a location where the thoracic wall has an increased thickness, whereby the doctor's attention can be called. Since the shape information of the extracted organ region is displayed on the screen, finding of an anomalous site by the doctor can be facilitated. The seventh embodiment has a peculiar effect in that, even in the case where automatic extraction of the reference regions or the organ regions is difficult because of presence of noise or the like on the axial image 71, the reference regions or the organ regions can be manually extracted on the basis of judgment by the operator.

Preferred embodiments of the image diagnosis support device according to the present invention have been described. However, the present invention is not limited to the above-described embodiments. It is clear that a person with ordinary skill in the art can easily conceive various modifications and changes within the technical idea disclosed herein, and it is contemplated that such modifications and changes naturally fall within the technical scope of the present invention.

The invention claimed is:

1. An image diagnosis support apparatus comprising:
   a display unit configured to display an image;
   a processing unit configured to control the image displayed by the display unit; and
   a non-transitory storage unit configured to store an image diagnosis support program including instructions executable by the processing unit,
   wherein the image diagnosis support program executable by the processing unit comprises:
      an image acquisition section configured for acquiring a tomographic thoracic image including an organ of interest of an object;
      a reference region extraction section configured for extracting a reference region representing a reference in the organ of interest from the tomographic thoracic image acquired by the image acquisition section;
      an organ region extraction section configured for extracting an organ region representing the organ of interest from the tomographic thoracic image acquired by the image acquisition section;
      an organ shape information calculation section configured for calculating organ shape information regarding the shape of the organ of interest from the reference region extracted by the reference region extraction section and the organ region extracted by the organ region extraction section; and a display control section configured for displaying on a display device the organ shape information calculated by the organ shape information calculation section, wherein the reference region extraction section extracts a rib region by performing threshold processing on the tomographic thoracic image, and extracts a reference line by interconnecting end portions of the rib region or end portion points near the end portions, and the organ shape information calculation section calculates for each specific point of plural reference line points that are on the reference line, a thickness of a thoracic wall, for an entirety of the thoracic wall, by performing a threshold processing from said each specific point towards a lung field.

2. An image diagnosis support device according to claim 1, wherein the organ region extraction section extracts the thoracic wall by performing threshold processing along lines which connect a centroid of the lung field and points on the reference line; and the organ shape information calculation section calculates the shape information regarding the thoracic wall on the basis of the extracted reference line and the extracted thoracic wall.

3. An image diagnosis support device according to claim 1, wherein the organ region extraction section extracts the thoracic wall by performing threshold processing in a passage region formed by translating the extracted reference line; and the organ shape information calculation section calculates the shape information regarding the thoracic wall on the basis of the extracted reference line and the extracted thoracic wall.

4. An image diagnosis support device according to claim 1, wherein the organ region extraction section extracts a region of the thoracic wall by performing threshold processing along lung-field-side normal lines of the reference line; and the organ shape information calculation section calculates the shape information regarding the thoracic wall on the basis of the extracted reference line and the extracted thoracic wall.

5. An image diagnosis support device according to claim 1, wherein the shape information regarding the thoracic wall includes at least one of a thickness, area, and volume of the thoracic wall.

6. An image diagnosis support device according to claim 1, wherein the reference region extraction section extracts the reference line by connecting the end portions of the rib region or the end portion points near the end portions by applying interpolation processing.

7. An image diagnosis support device according to claim 1, wherein the image diagnosis support program further comprises a warning section that performs warning processing when the organ shape information calculated by the organ shape information calculation section does not satisfy a predetermined condition.

8. An image diagnosis support device according to claim 7, wherein the warning section displays, on a medical image of the object displayed on the display apparatus, a region in which the organ shape information calculated by the organ shape information calculation section does not satisfy the predetermined condition, the area being displayed as an anomalous portion in an identifiable manner.

9. An image diagnosis support device according to claim 1, wherein the organ region extraction section extracts the organ region by performing threshold processing on the tomographic thoracic image.

10. An image diagnosis support device according to claim 9, wherein a threshold value for extracting the organ region from the tomographic thoracic image is set on the basis of a threshold value for extracting a bone region from the tomographic thoracic image.

11. An image diagnosis support device according to claim 1, wherein a threshold value for extracting the reference region from the tomographic thoracic image is set on the basis of a threshold value for extracting a bone region from the tomographic thoracic image.

12. An image diagnosis support device according to claim 1, wherein the image diagnosis support program further comprises a designation section that designates a designation point or a designation region which belongs to at least one of the reference region and the organ region on the tomographic thoracic image, wherein at least one of the reference region extraction section and the organ region extraction section extracts at least the reference region or the organ region on the basis of pixel values in the vicinity of the designation point or the designation region designated by the designation section.

13. An image diagnosis support program embodied in a non-transitory computer readable medium and including instructions executable by a computer to cause the computer to perform a method comprising:

(a) acquiring a tomographic thoracic image including an organ of interest of an object;

(b) extracting a reference region representing a reference in the organ of interest from the tomographic thoracic image acquired in (a);

(c) extracting an organ region representing the organ of interest from the tomographic thoracic image acquired in (a);

(d) calculating organ shape information regarding the shape of the organ of interest from the reference region extracted in (b) and the organ region extracted in (c); and (e) displaying on a display device the organ shape information calculated in (d), wherein the reference region is extracted in (b) by a process including extracting a rib region by performing threshold processing on the tomographic thoracic image, and extracting a reference line by interconnecting end portions of the rib region or end portion points near the end portions; and the organ shape information is determined in (d) by a process including calculating for each specific point of plural reference line points that are on the reference line, a thickness of a thoracic wall, for an entirety of the thoracic wall, by performing a threshold processing from said each specific point towards a lung field.

* * * * *